(12) United States Patent
Drasler et al.

(10) Patent No.: US 10,271,951 B2
(45) Date of Patent: Apr. 30, 2019

(54) MITRAL ANNULAR MEASUREMENT AND LVOT OBSTRUCTION TOOL

(71) Applicant: InterValve, Inc., Plymouth, MN (US)

(72) Inventors: William J. Drasler, Minnetona, MN (US); Wesley R. Pedersen, Minneapolis, MN (US)

(73) Assignee: InterValve Medical, Inc., Irvine, CA (US)

( * ) Notice: Subject to any disclaimer, the term of this patent is extended or adjusted under 35 U.S.C. 154(b) by 282 days.

(21) Appl. No.: 15/154,750

(22) Filed: May 13, 2016

(65) Prior Publication Data

US 2016/0331536 A1 Nov. 17, 2016

Related U.S. Application Data

(60) Provisional application No. 62/162,394, filed on May 15, 2015.

(51) Int. Cl.
| | |
|---|---|
| *A61F 2/24* | (2006.01) |
| *A61B 5/107* | (2006.01) |
| *A61B 5/00* | (2006.01) |
| *A61B 5/029* | (2006.01) |

(52) U.S. Cl.
CPC ......... *A61F 2/2496* (2013.01); *A61B 5/1076* (2013.01); *A61B 5/6869* (2013.01); *A61B 5/029* (2013.01); *A61F 2230/0063* (2013.01); *A61F 2250/0098* (2013.01)

(58) Field of Classification Search
CPC .... A61F 2/2496; A61B 5/1076; A61B 5/6869
USPC .......................................................... 600/587
See application file for complete search history.

(56) References Cited

U.S. PATENT DOCUMENTS

| | | | |
|---|---|---|---|
| 2007/0055338 A1* | 3/2007 | Dorn ......................... | A61F 2/95 623/1.11 |
| 2011/0112567 A1* | 5/2011 | Lenker .............. | A61M 25/0023 606/194 |
| 2011/0213460 A1* | 9/2011 | Lashinski .......... | A61B 17/0644 623/2.18 |
| 2012/0004577 A1* | 1/2012 | Saadat ................. | A61B 1/0008 600/587 |

* cited by examiner

Primary Examiner — Daniel L Cerioni
(74) Attorney, Agent, or Firm — Inskeep IP Group, Inc.

(57) ABSTRACT

A device is described for crossing the atrial septum to properly size a valve annulus for treatment or replacement, having a catheter with an expandable braided tubular structure attached at its distal end. The proximal and distal end regions of the braided tube have an open structure to allow blood flow to pass freely through the gaps or spaces between the braided fibers. The lumen within the tube includes a temporary, artificial valve that acts similar to a native valve, allowing blood to flow in one direction and preventing blood flow in the opposite direction.

16 Claims, 4 Drawing Sheets

MITRAL ANNULAR MEASUREMENT AND LVOT OBSTRUCTION TOOL

RELATED APPLICATIONS

This application claims priority to U.S. Provisional Application Ser. No. 62/162,394 filed May 15, 2015 entitled Mitral Annular Measurement and LVOT Obstruction Tool which is hereby incorporated herein by reference in its entirety.

BACKGROUND OF THE INVENTION

The present patent application makes reference to and fully incorporates all information found in U.S. Pat. No. 8,998,827 issued Feb. 13, 2013 entitled Ellipticity Measuring Device, and U.S. patent application Ser. No. 14/683,055 filed Apr. 9, 2015 entitled Post Dilation Balloon With Marker Bands For Use With Stented Valves.

Mitral regurgitation (MR) can occur due to a dysfunction of the mitral valve leaflets or due to enlargement of the left ventricle (LV) and mitral annulus causing mitral leaflets to no longer coapt properly. To correct MR, a surgical procedure can be performed to support the mitral annulus from further enlargement or to repair or replace the mitral valve leaflets.

An alternate procedure that is less invasive can be performed via a catheter that is introduced either across the atrial septum or through the apex of the heart. This mitral transvascular valve replacement (MTVR) procedure is intended to place a synthetic, tissue, or composite stented valve within the native mitral valve. Determining an accurate diameter for the MTVR device within the noncircular mitral annulus can be difficult and failure to make an accurate diameter determination can result in a paravalvular leakage of blood around the stented MTVR. In addition, the MTVR can impose an outward force onto the anterior native mitral valve leaflet causing it to obstruct the flow of blood from the LV out of the left ventricular outflow tract (LVOT).

What is needed is a device that can be easily inserted across the mitral valve annulus prior to implantation of an MTVR to determine an accurate diameter for the mitral annulus and can further be used to identify if the MTVR will impact onto the native anterior mitral valve leaflet resulting in obstruction to the LVOT.

SUMMARY OF THE INVENTION

The present invention is generally directed to a tool that can be introduced across the atrial septum or through the apex of the heart and across the mitral valve.

In one embodiment that can be used for crossing the atrial septum, a catheter has a braided tubular structure attached at its distal end to a pull tube that passes through a catheter shaft; the proximal end of the tubular braid is attached to the outer shaft of the catheter. The proximal and distal end regions of the braided tube have an open structure to allow blood flow to pass freely through the gaps or spaces between the braided fibers. The central or middle region of the braided tube located in the central third of the braided structure has an elastomeric film that connects the braided fibers with their neighboring fibers to form a fluid-tight region. Located within the central region is a temporary valve that unidirectionally prevents blood flow through the lumen of the central region, similar to a native valve. The temporary valve is attached to the braided tubular structure along the perimeter of the braided tube in a manner similar to the attachment of an aortic valve leaflet to the aortic sinus or a venous valve leaflet to the tubular structure of a vein wall of the body. The temporary valve leaflets form a seal with other leaflets and also against the outer surface of the pull tube.

The tool can be advanced across a patient's mitral valve with the pull tube pushed distally with respect to the outer shaft to hold the braided tubular structure into a small diameter state having a long length. After crossing the mitral valve, the pull tube can be pulled with respect to the outer shaft to cause the braided structure to enlarge in diameter and shorten in length and thereby push the native mitral leaflets outwards and make contact with the mitral annulus. With the braided structure expanded in diameter, the temporary valve will function to ensure that blood is not able to pass freely from the LV back into the left atrium (LA). Blood is able to pass freely from the LA through the proximal end region of the braided structure, across the temporary valve leaflets, and out of the distal end region of the braided structure into the LV. Examination of the braided structure under fluoroscopy will enable the operator to determine the diameter of the mitral annulus; further examination of the LVOT will allow the operator to determine if the anterior native leaflet is impinging upon the LVOT.

The tool can be altered to allow its introduction from an apical approach; in this embodiment the temporary valve leaflets are directed to provide flow from the distal end of the braided structure toward the proximal end of the braided structure toward the direction of the catheter shaft.

In an alternate embodiment for the tool, the braided tubular structure can have a bulbous shape such that a waist exists within the tubular structure having a smaller diameter by about 3-10 mm than the bulbous portions of the braided structure that are located on each side of the waist. The waist can be held into a smaller diameter configuration during the expansion of the braid by a restraining fiber that extends around the perimeter of the braided tube. The restraining fiber can be, for example, an elastic fiber that can stretch as the waist grows in diameter but serves to hold the waist into a smaller diameter than the bulb regions; alternately a geometric shape that is able to expand in length can be used as the restraining fiber; such structures include the zig zag structure commonly used in vascular stents, or can be a cable that is easily bent but having tensile strength that will prevent diameter enlargement of the waist.

As a further alternate embodiment, the waist can be formed via thermal processing that places a bulbous shape into the braided tubular structure. The waist will tend to orient adjacent the annulus of the mitral valve. Located adjacent the restraining fiber is a marker band or alternately the restraining fiber is the marker band. The marker band can be formed from a radiopaque (RO) material that is visualized under fluoroscopy or from a material observable under echogenic signals. The marker band can be formed by embedding RO material into an elastic carrier polymer and applying the polymer or the band onto the waist region or other region of the braided tubular structure. Additional marker bands can be located on one or more of the bulbs.

After placing this tool across the mitral valve, the braided structure is expanded. The waist of the braided structure centers adjacent the mitral annulus. The waist marker band can be visualized to determine the diameter of the mitral annulus and also to assess the roundedness, ovality, or "D" shape of the mitral annulus. One or more of the bulb marker bands can be visualized to assess a circular shape that can be used as a reference to establish the true shape of the mitral annulus. The tool can also be used to identify if impingement is being generated by the anterior mitral leaflet onto the LVOT.

In yet another embodiment a tubular balloon can be formed into a spiral shape to cross the native mitral valve and determine if impingement of the anterior mitral leaflet onto the LVOT is anticipated. The spiral balloon is formed such that a central lumen is open to blood flow from the left atrium (LA) to the left ventricle (LV). A temporary valve located in the central lumen ensures that blood flow from the LV cannot pass retrograde from the LV to the LA. The edges of the balloon spiral are attached to neighboring spirals to prevent leakage of blood from the central lumen across the spiral balloon.

The spiral balloon can be formed such that it contains a waist region that forms a smaller diameter spiral than one or more bulbous regions located adjacent or on each side of the waist. Marker bands can be placed onto the outer surface of the spiral balloon that can be visualized under either fluoroscopy or via echogenic signals.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1B:
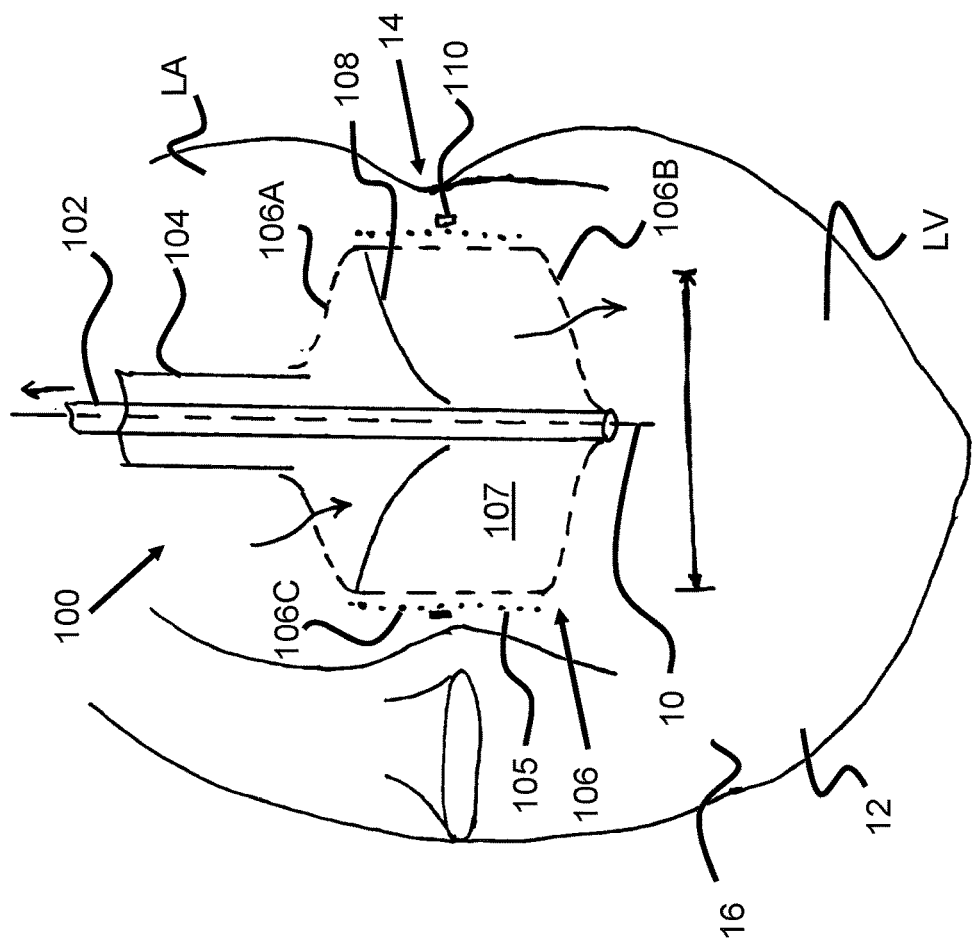
FIG. 1B is a sectional view of the tool in an expanded configuration within the mitral annulus from the left atrium.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1A:
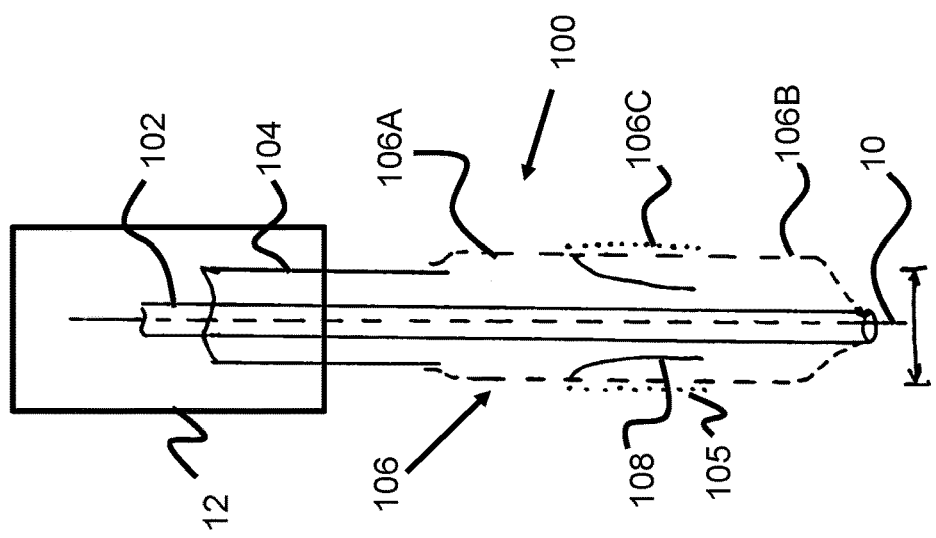
FIG. 1A is a sectional view of the tool in a non-expanded configuration.

FIGS. 1A-1B illustrate a tool 100 that is placed or positioned across the mitral annulus 14 prior to placing a transcatheter mitral valve replacement (TMVR) device. The tool 100 can be visualized under fluoroscopy to determine the diameter of the mitral annulus. Further, the tool 100 interfaces with the native mitral valve leaflets causing them to be pushed outwards such that any obstruction of the left ventricular outflow tract (LVOT) 16 by the native anterior mitral leaflet can be visualized under fluoroscopy and adjustment can be made in the diameter and length of the TMVR that is implanted across the mitral annulus.

FIG. 1A illustrates the tool 100 in an unexpanded configuration having a relatively smaller, unexpanded diameter to allow entry and passage through a sheath 12. The sheath 12 is advanced within the femoral vein so as to allow delivery of the tool 100 through the atrial septum and across the mitral annulus 14.

Generally, tool 100 has an expandable portion 106, having open mesh portions, such as proximal mesh portions 106A and distal mesh portion 106B, which allow blood to flow within the expandable portion 106. An artificial valve 108 composed of valve leaflets are located within the expandable portion 106 and allow passage of blood through the expandable portion 106 in a single direction, similar to a native valve (e.g., in a distal direction in the current example).

In one embodiment, the expandable portion 106 is constructed of a braided or expandable metal tube that is bonded at its proximal end to the outer shaft 102, near the distal end of the outer shaft 104. The braided or expandable tube portion 106 can be formed from wire composed of Nitinol (NiTi), stainless steel, or other material that allows expansion to a larger diameter as its length becomes shorter.

The distal end of the braided tubular member 106 is preferably bonded to a distal end of a hollow pull tube 102 that moves relative to the outer shaft 104. Movement of the pull tube 102 with respect to the outer shaft 104 by application of tension on the pull tube 102 by the physician causes the braided tube 106 to shorten in length as it grows in diameter.

The central region 106C of the braided tube 106 has an elastomeric film 105 such as polyurethane or silicone applied to the braided fibers and extending across the gaps or spaces that extend from one fiber of the braid to the neighboring fibers. The film 105 prevents the flow of fluid such as blood through the spaces between the fibers in the central region which extends approximately along the central third of the braided tube 106. The film 105 prevents blood flow from traveling from the lumen 107 of the braided tubular structure 106 to an outer region that is located outside of the braided tubular structure 106 and adjacent to the valvular tissues and the other tissues of the heart.

The central region 106C contains a temporary, artificial valve 108 that directs blood flow downstream from the proximal open mesh 106A to the distal end 106B of the braided tube 106 (i.e., it allows blood flow in a distal direction but prevents backflow in a proximal direction). The temporary leaflets 108 can be formed from a tissue material or a synthetic polymer film, such as polyethylene terephthalate (PET) or Nylon, that is formed into a trileaflet or bileaflet valve such as those found within the human body. The leaflets of the valve 108 are attached to the elastomeric film 105 in the central region 106C forming a crown-shaped attachment to the central region 106C similar to the attachment of a native tricuspid valve leaflet of the aortic valve or a bicuspid leaflet of a venous valve.

The proximal end region 106A has an open spacing between the fibers or wires of the braided tube to allow blood to travel from the left atrial chamber or left atrium (LA) of the heart into the lumen of the braided tubular structure; the distal end region has an open spacing to allow flow from the lumen of the braided tubular structure to the left ventricle (LV). The hollow pull tube 102 provides passage for a guidewire 10 for delivery of the device 100 across the mitral valve 14.

As shown in FIG. 1B the pull tube 102 has been moved proximally relative to the outer tube 104, causing the distal end 106B of the braided tube 106 to move closer to the proximal end 106A and thereby causing the diameter of the braided to tube 106 to enlarge. This enlargement of the braided tube 106 causes the braided structure 106 to make contact with the native mitral leaflets pushing them outwards, and make contact with the mitral annulus. The braided structure 106 and particularly radiopaque markers 110 can then be observed under fluoroscopy to allow measurement of the diameter of the mitral annulus. The movement of the native anterior mitral leaflet into the LVOT 16 will establish if placement of an MTVR device will result in anterior leaflet obstruction of the LVOT 16.

Figure 1C:
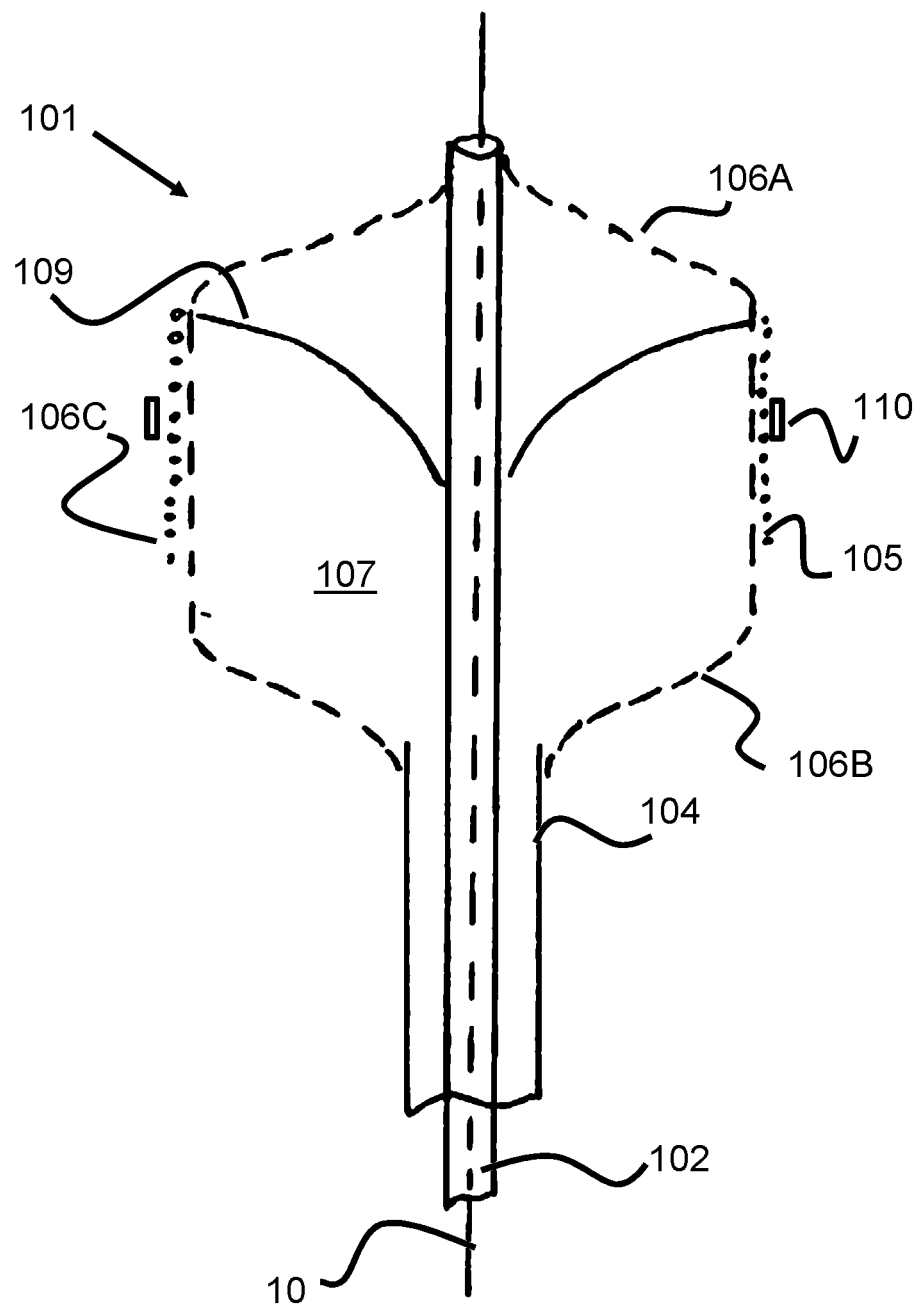
FIG. 1C is a sectional view of the tool in an expanded configuration if the tool is entered from the apex of the heart.

FIG. 1C illustrates an alternate version 101 of the device 100 used for insertion via an apical approach rather than from the femoral vein. In this respect, the direction of the leaflets of the temporary valve 109 located within the lumen 107 of the braided tubular structure 106 open in an opposite direction than those of device 100. In other words, the valve 109 allows blood flow to move proximally since it is generally positioned in an "upside-down" position verses the device 100. However, the mode of action for this tool is similar to that described for the device 100 of FIG. 1B.

Figure 2:
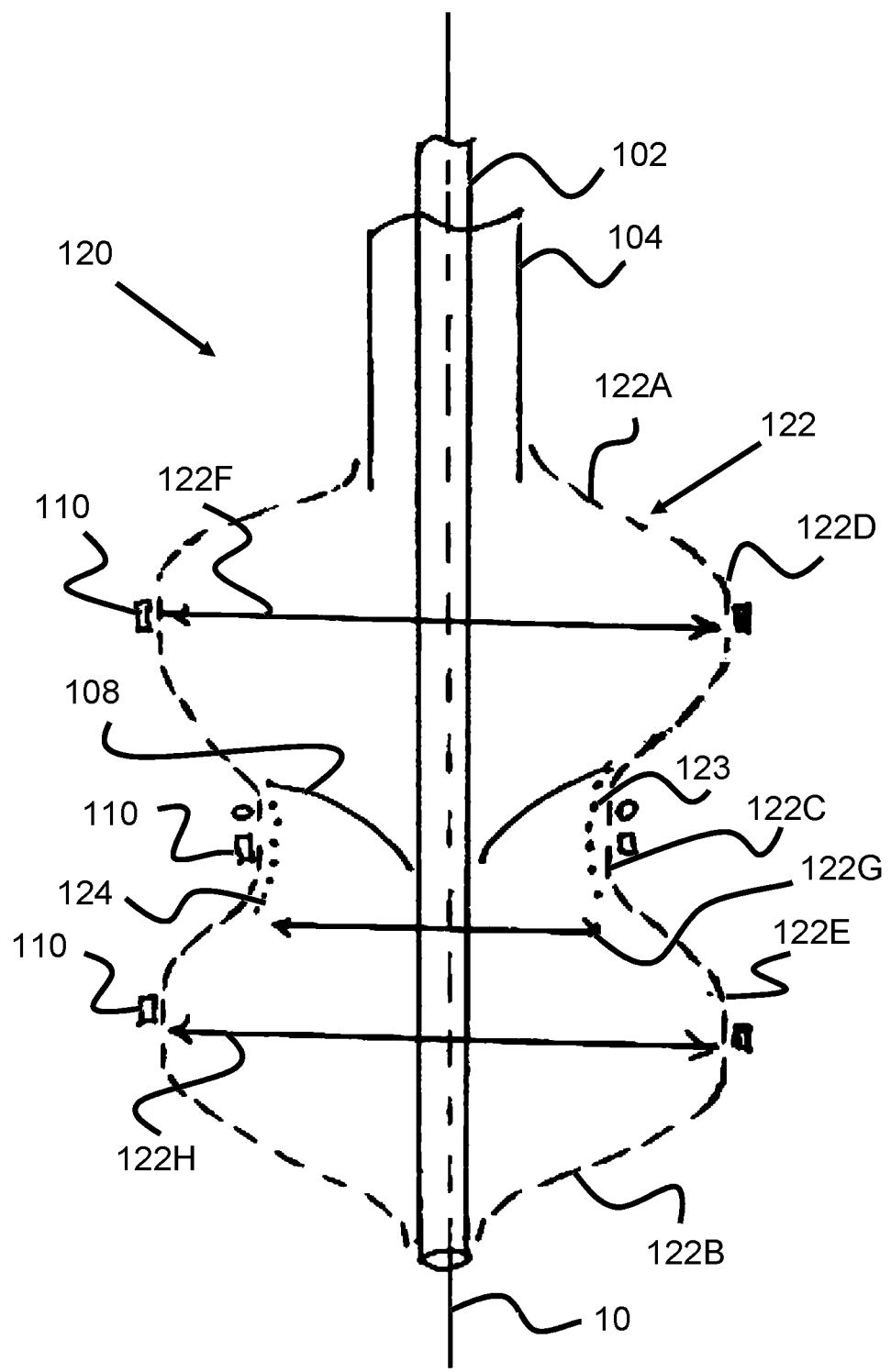
FIG. 2 is a sectional view of the tool in an expanded configuration having a smaller diameter waist and larger diameter bulbs.

FIG. 2 illustrates an embodiment 120 for the present invention similar to the devices 100 and 101 described in FIGS. 1A-1C, having a pull tube 102, an outer tube 104, a temporary valve 108, and a braided tubular structure 122 having a proximal end 122A and a distal end 122B through which blood flows. However, the tubular structure 122 expands to a "dog bone" shape or a shape having a proximal bulb 122D with a diameter 122F, a waist 122C with a diameter 122G, and a distal bulb 122E with a diameter 122H. A restraining fiber 123 formed from a polymer or metal material can be used to restrict the waist diameter to a magnitude that is, for example, approximately 3-10 mm smaller than the diameter of the proximal or distal bulbs 122A, 122B. The waist can alternately be formed via thermal processing of an elastic metal such as Nitinol, for example. The bulb diameters in a fully expanded configuration can be approximately 3-10 mm larger than an effective diameter of the mitral annulus. The mitral annulus is typically D-shaped with an effective diameter (equal to the diameter of a circle having the same perimeter) of 25-45 mm.

Located along the perimeter of the waist 122C of the braided structure 106 is a marker band 110 such as a radiopaque (RO) marker or an echo-sensitive marker. The echo-sensitive marker can be a marker that absorbs, reflects, generates, or scatters echogenic energy that is delivered via a cardiac echo transducer to visualize the structures of the heart. The RO marker can be formed from materials that absorb x-rays such as tungsten, platinum, platinum-iridium and others. An echo-sensitive marker or RO marker can also be located on one or both of the bulbs. Visualization of the RO or echo-sensitive marker under fluoroscopy or echo will allow the operator to observe the shape and diameter of the mitral annulus. The marker 110 located along one of the bulbs is typically round in shape along its perimeter and can serve as a reference to identify the angle of the fluoro or echo camera and any magnification factor associated with the diameter of the bulb. The marker 110 located along the perimeter of the waist can then be used to identify the diameter and shape of the mitral annulus as described further in the patents that are referenced herein.

The device 120 of FIG. 2 also can be used in a manner similar to that described for the devices 100 and 101 of FIGS. 1A-1C to identify if a subsequently placed MTVR is likely to obstruct the LVOT. The structure of the braided tube 122, the temporary valve 108, the film 105 located in the central region 122C is similar to that described in FIGS. 1A-1C.

The method of use for the embodiments of the tool shown in FIGS. 1-3 are herein described. The tool is delivered across the mitral annulus from either the left atrium or via the left ventricular apex in a small diameter configuration. The pull tube is placed into tension causing the braided mesh to expand in diameter pushing the native mitral leaflets outward to the side. The temporary leaflets located near the central region of the tool prevent blood flow from retrograde flow from the left ventricle to the left atrium. The elastic film located adjacent the temporary leaflets and attached to the central region of the mesh prevent blood flow from forming a perivalvular leak for blood flow around the temporary leaflets. The braided mesh in the central region is pushed against the mitral annulus; the presence of a marker band allows the operator to measure the diameter of the mitral annulus. The braided mesh located in the left ventricle pushes outward against the anterior native mitral valve leaflet pushing the native leaflet into the left ventricular outflow tract (LVOT). Fluoroscopy is used by the operator to view potential for obstruction of the LVOT from the native leaflet. If obstruction is observed, the subsequent transcatheter mitral valve replacement (TMVR) procedure may require some adjustment in the type of TMVR device to use or else cancel the TMVR procedure. Alternately, if no obstruction is observed, then the TMVR procedure is performed with knowledge apriori that obstruction is not of concern for than patient. Following measurement of mitral annulus diameter and determination of obstruction of the LVOT, the braided mesh is reduced in diameter by the operator to a smaller introduction diameter and the catheter is removed from the body.

Figure 3A:
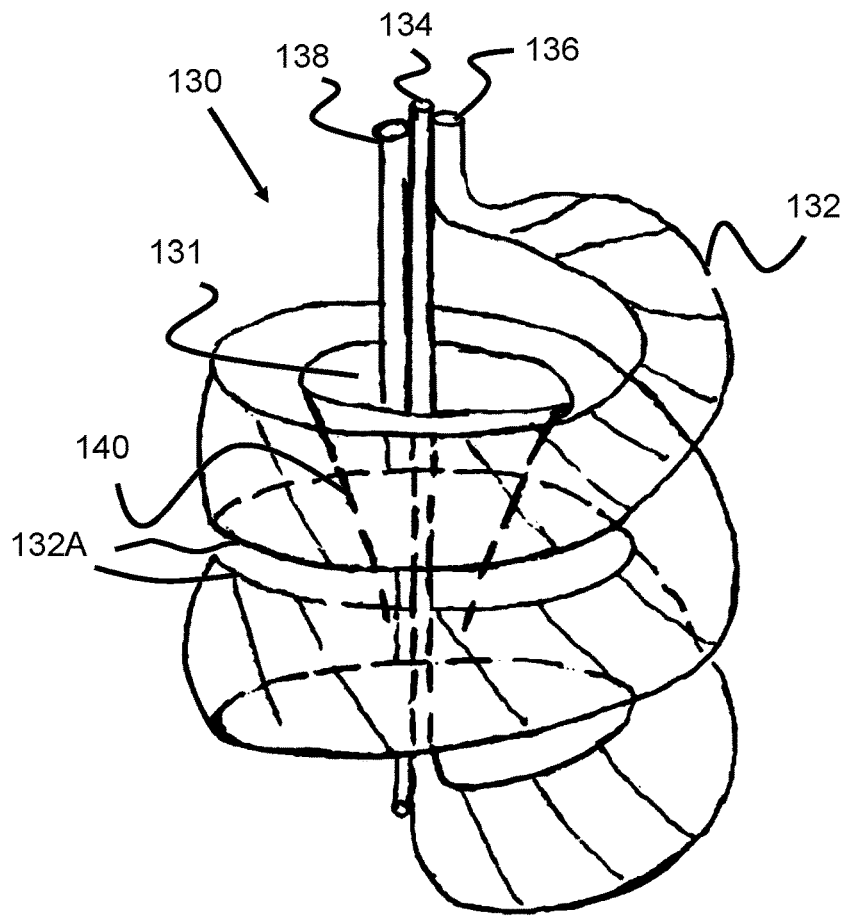
FIG. 3A is a perspective view of the tool formed from a spiral wound tubing.
Figure 3B:
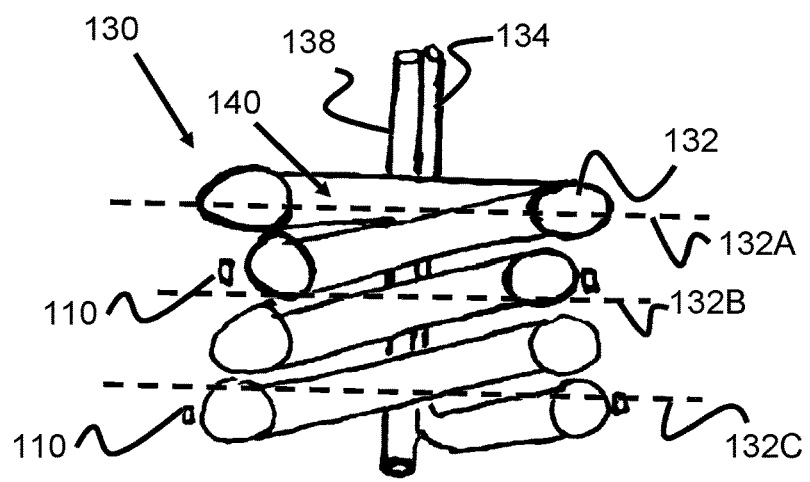
FIG. 3B is a perspective view of the tool formed from a spiral wound tubing and having a smaller diameter waist and larger diameter

FIGS. 3A and 3B illustrate another embodiment for a tool 130 of the present invention that can be placed across the mitral annuls in a similar manner as the previously described embodiments. In this embodiment, the device 120 includes an elongated, helical balloon 132 having a diameter of approximately 0.5-1 cm. The balloon 132 is wound into a spiral shape having a diameter for the spiral of approximately 25-45 mm in an inflated configuration. A central through lumen 131 provides a channel for blood flow from the LA to the LV. The spirals of the spiral balloon 132 are preferably bonded to their neighboring spiral along an edge such that blood flow through or between the spirals is prevented.

A temporary valve 140 is located in the central lumen to allow flow from the LA to the LV and restrict flow from the LV to the LA. The tool can be delivered across the mitral annulus in a small diameter configuration and inflated with contrast or other fluid to form a fully inflated configuration as shown in FIGS. 3A and 3B. The diameter of the mitral annulus can be view upon fluoroscopic examination. As shown in FIG. 3B the spiral loop can be formed such that it contains a waist region 132B having a smaller diameter than either bulbous regions 132A, 132C. A marker band 110 can be located along the perimeter of the waist 132B to allow improved visualization of the diameter and shape of the mitral annulus. A marker band 110 can also be located around the perimeter of one or both bulbs 132A, 132C to serve as a diameter reference and also to identify the angle of fluoroscopy camera or echo camera with respect to the axis of the spiral balloon. A guidewire lumen 138 can also be located along the axis of the spiral balloon 132 to assist in delivery of the device across the mitral annulus. The balloon 132 can be connected to a single inflation tube 136 at its proximal end and/or to a second inflation tube 134 connected to a distal end of the balloon 132.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A device for measuring the diameter of a mitral annulus and evaluating obstruction to flow in the left ventricular outflow tract comprising:
   A. a catheter having an outer shaft and an inner pull tube located within said outer shaft,
   B. a braided tubular structure located at the distal end of said catheter, a distal end of said braided tubular structure being bonded to a distal end of said inner pull tube, a proximal end of said braided tubular structure being bonded to a distal end of said outer shaft,
   C. a central region of said braided tubular structure having an elastomeric film attached thereto forming a fluid barrier for fluid transfer from a lumen of said braided tubular structure to an outer region located outside of said braided tubular structure,
   D. a proximal end region of said braided tubular structure having an open braided structure that allows fluid transfer from outside of said braided structure to said lumen of said braided structure and a distal end region of said braided tubular structure that allows transfer of fluid from said lumen of said braided tubular structure to outside of said braided tubular structure,
   E. said central region containing a temporary valve,
   F. the braided tubular structure bonded to the inner pull tube has a first diameter when the distal end of the inner pull is located in a first distance from the distal end of the outer shaft, and has a second diameter larger than the first diameter when the distal end of the inner pull is located in a second distance from the distal end of the outer shaft, wherein the second distance is shorter than the first distance.

2. The device of claim 1 wherein said central region of said braided tubular structure contains a waist, said waist having a smaller diameter than a proximal bulb of said proximal end region and a smaller diameter than a distal bulb of said distal end region.

3. The device of claim 1 wherein said central region comprises a marker band that is able to be visualized under fluoroscopy.

4. The device of claim 2 wherein said proximal bulb or said distal bulb comprise a marker band that is able to be visualized under fluoroscopy.

5. The device of claim 3 wherein said marker band is formed from an elastic material that allow said marker band to enlarge in diameter to equal the diameter of the braided tubular structure.

6. The device of claim 2 wherein said braided tubular structure is formed from an elastomeric material that is thermally formed into a shape that provides said waist with a smaller diameter than said proximal and distal bulbs.

7. The device of claim 1 wherein the distal end of the braided tubular structure is bonded to the inner pull tube along a periphery of the distal end, and the proximal end of the braided tubular structure is bonded to the outer shaft along a periphery of the distal end.

8. The device of claim 1 wherein the braided tubular structure is configured to shorten in length and expand in diameter with movement of the distal end of the inner pull tube towards the distal end of the outer shaft.

9. The device of claim 1 wherein the inner pull tube is positioned coaxially within the lumen of the braided tubular structure and the temporary valve abuts against an outer surface of the inner pull tube.

10. The device of claim 1 wherein the distal end region and the proximal end region of the braided tubular structure are transverse to a longitudinal axis of the inner pull tube in an expanded state of the braided tubular structure.

11. The device of claim 1 wherein each of the distal end region and the proximal end region has an inner surface facing to the lumen of the braided tubular structure, wherein the inner surface of the distal end region and the inner surface of the proximal end region face to each other in an expanded state of the braided tubular structure.

12. The device of claim 2 wherein a retaining fiber extending around the waist of the braided tubular structure is provided, the retaining fiber being configured to prevent enlargement of the diameter of the waist.

13. A device for measuring the diameter of a mitral annulus and evaluating obstruction to flow in the left ventricular outflow tract comprising:
   A. a catheter having an outer shaft and an inner pull tube located within said outer shaft,
   B. a braided tubular structure located at the distal end of said catheter, a distal end of said braided tubular structure being bonded to a distal end of said inner pull tube, a proximal end of said braided tubular structure being bonded to a distal end of said outer shaft,
   C. a central region of said braided tubular structure having an elastomeric film attached thereto forming a fluid barrier for fluid transfer from a lumen of said braided tubular structure to an outer region located outside of said braided tubular structure,
   D. a proximal end region of said braided tubular structure having an open braided structure that allows fluid transfer from outside of said braided structure to said lumen of said braided structure and a distal end region of said braided tubular structure that allows transfer of fluid from said lumen of said braided tubular structure to outside of said braided tubular structure,
   E. said central region containing a temporary valve,
   F. the braided tubular structure is configured to shorten in length and expand in diameter with movement of the distal end of the inner pull tube towards the distal end of the outer shaft.

14. The device of claim 13 wherein the inner pull tube is positioned coaxially within the lumen of the braided tubular structure and the temporary valve abuts against an outer surface of the inner pull tube.

15. The device of claim 13 wherein the distal end region and the proximal end region of the braided tubular structure are transverse to a longitudinal axis of the inner pull tube in an expanded state of the braided tubular structure.

16. The device of claim 13 wherein each of the distal end region and the proximal end region has an inner surface facing to the lumen of the braided tubular structure, wherein the inner surface of the distal end region and the inner surface of the proximal end region face to each other in an expanded state of the braided tubular structure.

* * * * *